United States Patent [19]

King et al.

[11] 3,956,478

[45] May 11, 1976

[54] DENTIFRICE COMPOSITION

[75] Inventors: William James King, River Edge; Leo Thomas Murray, East Brunswick; Gerhard Martin Salzmann, Franklin Lakes, all of N.J.

[73] Assignee: Colgate-Palmolive Company, New York, N.Y.

[22] Filed: May 6, 1975

[21] Appl. No.: 575,021

Related U.S. Application Data

[60] Division of Ser. No. 471,378, May 20, 1974, which is a continuation-in-part of Ser. No. 176,396, Sept. 9, 1971, Pat. No. 3,864,471, which is a continuation of Ser. No. 848,241, Nov. 16, 1969, abandoned, which is a continuation-in-part of Ser. No. 785,731, Dec. 20, 1968, abandoned.

[52] U.S. Cl. ............................... 424/52; 424/49; 424/57
[51] Int. Cl.² ............................................. A61K 7/18
[58] Field of Search ............................... 424/49–58

[56] References Cited

UNITED STATES PATENTS

| | | | |
|---|---|---|---|
| 3,060,098 | 10/1962 | Gershon | 424/52 |
| 3,119,743 | 1/1964 | Ericsson | 424/52 |
| 3,227,617 | 1/1966 | Manahan et al. | 424/52 |
| 3,227,618 | 1/1966 | Manahan et al. | 424/52 |
| 3,634,585 | 1/1972 | Manahan et al. | 424/52 |

*Primary Examiner*—Shep K. Rose
*Attorney, Agent, or Firm*—Robert L. Stone; Murray M. Grill; Herbert S. Sylvester

[57] ABSTRACT

Dentifrice composition containing a monofluorophosphate and polishing agent containing calcium carbonate and insoluble alkali metal metaphosphate, alumina or mixture thereof. The ratio of calcium carbonate to insoluble alkali metal metaphosphate and to alumina is about 3:1 to about 1000:1. This dentifrice retains a desirable level of soluble fluoride upon aging and when insoluble alkali metal metaphosphate is present, does not cause substantial corrosion of unlined aluminum containers.

6 Claims, No Drawings

DENTIFRICE COMPOSITION

This application is a divisional of Ser. No. 471,378 filed May 20, 1974 which is a continuation-in-part of Ser. No. 176,396 filed Sept. 9, 1971, now U.S. Pat. No. 3,864,471 issued Feb. 4, 1975 which was filed as a continuation of Ser. No. 848,241, filed Nov. 19, 1969, now abandoned, which was filed as a continuation-in-part of Ser. No. 785,731, filed Dec. 20, 1968, now abandoned.

The present invention relates to a dentifrice preparation containing a water-soluble monofluorophosphate salt.

Water soluble monofluorophosphates and particularly alkali metal monofluorophosphates such as sodium monofluorophosphate have been used as fluorine-providing active ingredients in dentifrice compositions. The polishing agents which may be used in such dentifrices have been the subject of much investigation.

A dentifrice containing sodium monofluorophosphate and a polishing agent which is free of insoluble phosphate salt and which, in fact, is solely calcium carbonate loses an appreciable amount of the fluorine in solution upon aging.

In order to obtain maximum fluorine-retention of the monofluorophosphate, the prior art has used minor amounts of calcium salt, such as dicalcium phosphate or calcium carbonate, or magnesium salt, and has used as the major polishing agent, insoluble alkali metal metaphosphate. It has been the general practice in the prior art to package monofluorophosphate dentifrices in an epoxy lined aluminum container or in lined containers of other metals or in plastic containers since components of various monofluorophosphate dentifrices cause corrosion of unlined aluminum tubes upon storage.

This invention provides monofluorophosphate dentifrice which has special advantages over prior art monofluorophosphate dentifrices containing calcium carbonate or insoluble alkali metal metaphosphate. More particularly, the dentifrice of the instant invention eliminates the instability characteristic of prior art monofluorophosphate dentifrice containing calcium carbonate which is free of insoluble phosphate. The invention also provides a monofluorophosphate dentifrice which upon storage does not cause substantial corrosion of unlined aluminum containers.

Other desirable properties will be apparent from consideration of the following specification.

In accordance with certain of its aspects, this invention relates to a dentifrice composition comprising a water-soluble monofluorophosphate and a water-insoluble compatible polishing material comprising a mixture of calcium carbonate and insoluble alkali metal metaphosphate, the ratio of said carbonate to said insoluble alkali metal metaphosphate being about 3:1 to about 1000:1.

Such a dentifrice retains a desirable high level of monofluorophosphate as fluoride upon aging and can also be compatibly incorporated into unlined aluminum tubes.

The sodium monofluorophosphate as commercially available may vary considerably in purity. It may be used in any suitable purity provided that any impurities do not substantially adversely affect the desired properties. In general, the purity is desirably at least about 80%. For best results, it should be at least 85%, and preferably at least 90% by weight of sodium monofluorophosphate with the balance being primarily impurities or by-products of manufacture such as sodium fluoride, water-soluble sodium phosphate salt, and the like. Expressed in another way, the sodium monofluorophosphate employed should have a total fluoride content of above 12%, preferably above 12.7%; a content of not more than 1.5%, preferably not more than 1.2% of free sodium fluoride; and a sodium monofluorophosphate content of at least 12% preferably at least 12.1%, all calculated as fluorine.

Typically, the monofluorophosphate is present in amount which provides about 0.01–1% fluorine to the dentifrice. Sodium monofluorophosphate may be present in amounts of about 0.05% to about 7.6%.

The calcium carbonate of the polishing agent is preferably chalk. Chalk is typically employed in powder form of a size of about 1 to 10 microns.

It is preferred to use a grade of calcium carbonate of relatively high apparent specific gravity, say about 0.9 to 1.2. If desired, calcium carbonate grades of lower apparent specific gravity, say about 0.7 to 0.9, also may be used. "Apparent specific gravity" refers to the untamped specific gravity of salt.

In accordance with certain aspects of this invention, the minor component of the polishing agent is an insoluble alkali metal metaphosphate.

The insoluble alkali metal metaphosphates are preferably the insoluble sodium and potassium salts of polymetaphosphoric acid. These materials are known in the art with the insoluble sodium metaphosphate having been suggested as a polishing agent as previously indicated. Such materials may be formed in any suitable manner, as illustrated by Thorpe's Dictionary of Applied Chemistry, vol. 9 (4th ed.), pp. 510–511. The forms of insoluble sodium metaphosphate known as Madrell's salt and Kurrol's salt are further examples of suitable materials. These metaphosphate salts exhibit only a minute solubility in water, and are commonly referred to as insoluble metaphosphates therefore. There is present a minor amount of soluble phosphate material as impurities, usually of the order of a few percent such as up to about 4% by weight. The amount of soluble phosphate material which is believed to be a soluble sodium trimetaphosphate in the case of insoluble sodium metaphosphate may be reduced by washing with water if desired. The insoluble alkali metal metaphosphate is typically employed in powder form of a size such that no more than about 1% of the material is larger than about 37 microns.

The ratio of calcium carbonate to insoluble alkali metal metaphosphate is about 3:1 to about 1000:1, preferably about 6:1 to about 1000:1, say, about 6:1 to about 500:1, and most preferably about 46.25:1.

At the preferred ratios, particularly when relatively small amounts of insoluble alkali metal metaphosphate are employed, the dentifrice does not corrode unlined aluminum tubes, almost without exception. When greater amounts of the metaphosphate are employed, within the scope of the invention, the dentifrice still does not cause substantial corrosion of unlined aluminum tubes, although an exceptional case of some adverse action on the aluminum may occasionally occur.

The total polishing agent content of the dentifrice is variable, but will generally be up to about 95%, by weight of the total composition. In the case of a dental cream, such polishing agents will generally be about 20% to about 75%, whereas in tooth powders the polishing agents will usually be in greater proportion, such as about 70% to about 95%.

In the preparation of tooth powders, it is usually sufficient to admix mechanically, for example, by milling, the various solid ingredients, in appropriate quantities and particle sizes.

Any suitable surface active or detersive material may be included in the dentifrice compositions. Such compatible materials are desirable to provide additional detersive, foaming and anti-bacterial properties depending upon the specific type of surface active material and are selected similarly. These detergents are water-soluble organic compounds usually, and may be anionic, nonionic or cationic in structure. It is preferred to use the water-soluble non-soap or synthetic organic detergents usually. Suitable detersive materials are known and include, for example, the water-soluble salts of higher fatty acid monoglyceride monosulfate detergent (e.g. sodium coconut fatty acid monoglyceride monosulfate), higher alkyl sulfate (e.g. sodium lauryl sulfate), alkyl aryl sulfonate (e.g. sodium dodecyl benzene sulfonate), higher fatty acid esters of 1,2-dihydroxy propane sulfonate (e.g. sodium coconut fatty acid ester of 1,2-dihydroxy propane sulfonate), and the like.

The various surface active materials may be used in any suitable amount, generally from about 0.05 to about 10% by weight, and preferably from about 0.5 to 5% by weight of the dentifrice composition.

It is a further embodiment of the present invention to use the substantially saturated higher aliphatic acyl amides of lower aliphatic amino carboxylic acid compounds, such as those having 12 to 16 carbons in the acyl radical, and as more particularly described in U.S. Pat. No. 2,689,170, issued Sept. 14, 1954. The amino acid portion is derived generally from the lower aliphatic saturated monoaminocarboxylic acids having about 2 to 6 carbons, usually the monocarboxylic acid compounds. Suitable compounds are the fatty acid amides of glycine, sarcosine, alanine, 3-aminopropanoic acid and valine having about 12 to 16 carbons in the acyl group. It is preferred to use the N-lauroyl, myristoyl and palmitoyl sarcoside compounds however for optimum effects.

The amide compounds may be employed in the form of the free acid or preferably as the water-soluble salts thereof, such as the alkali metal, ammonium, amine and alkylolamine salts. Specific examples thereof are sodium and potassium N-lauroyl, myristoyl and palmitoyl sarcosides, ammonium and ethanolamine N-lauroyl sarcoside, N-lauroyl sarcosine, and sodium N-lauroyl glycide and alanine. For convenience herein, reference to "amino carboxylic acid compound", "sarcoside", and the like refers to such compounds having a free carboxylic group or the water-soluble carboxylic salts.

Such materials are utilized in pure or substantially pure form. They should be as free as practicable from soap or similar higher fatty acid material which tends to reduce the activity of these compounds. In usual practice, the amount of such higher fatty acid material is less than 15% by weight of the amide and insufficient to substantially adversely affect it, and preferably less than about 10% of said amide material.

In dental cream formulations, the liquids and solids should be proportioned to form an extrudable creamy mass of desirable consistency. In general, liquids in the dental cream will comprise chiefly water, glycerine, sorbitol, propylene glycol, or the like, including suitable mixtures thereof. It is advantageous usually to use a mixture of both water and a humectant such as glycerine or sorbitol. It is preferred to use glycerine. The total liquid content will generally be about 20–75% by weight of the formulation. It is preferred to use also a gelling agent in dental creams such as the natural and synthetic gum and gum-like material, e.g. Irish moss, gum tragacanth, sodium carboxymethylcellulose, polyvinylpyrrolidone, starch and the like. The Irish moss and sodium carboxymethylcellulose are compatible particularly and are preferred gelling agents as illustrated. The gum content is usually in an amount up to about 10% and preferably about 0.5–5% by weight of the formulation.

In accordance with certain aspects of this invention, desirable aging characteristics are obtained when a minor amount of hydrated aluminum oxide (alumina) is in the dentifrice preparation as part of the polishing agent together with calcium carbonate. The ratio of carbonate to alumina is about 3:1 to about 1000:1. If desired, insoluble alkali metal metaphosphate may also be a component of the polishing agent. The ratio of the carbonate to insoluble alkali metal metaphosphate also being about 3:1 to about 1000:1. Dentifrices containing small amounts of insoluble alkali metal metaphosphate, say where the ratio of calcium carbonate to the metaphosphate is more than 100:1, have better aging characteristics when alumina is also present.

A dental cream having improved physical properties may be prepared from calcium carbonate and optionally insoluble alkali metal metaphosphate suspended in a gel comprising water, humectant and gelling agent, with said fluoride compound and organic non-soap synthetic detergent, and hydrated aluminum oxide, said dental cream having pH from about 7 to 9.5. If insoluble alkali metal metaphosphate is present, the hydrated aluminum oxide may be omitted. These dental creams exhibit a superior degree of stability to aging for long periods of time, particularly at elevated temperatures. The aluminum oxide acts as a stabilizing and modifying agent so as to eliminate or inhibit any tendency for separation or syneresis of the dental cream in the collapsible tube.

The preferred ratio of calcium carbonate to alumina is about 3:1 to 100:1, and most preferably about 35:1 to about 52:1.

In the instant invention sufficient insoluble alkali metal metaphosphate and/or alumina is present to substantially prolong the period of time during which the monofluorophosphate remains substantially soluble, e.g., to insure that at least, and preferably more than, about 40%, and most preferably at least 50% of the original monofluorophosphate content remains soluble after accelerated aging of the dentifrice for 9 weeks at 49°C.

Suitable examples of hydrated aluminum oxide which may be employed are the forms known as alpha and beta aluminum oxide trihydrate and mixtures thereof. It is used usually in the form of fine particles of any desired particle size in the manufacture of the dental cream. In practice, it is preferred to use the alpha trihydrate form of which at least about 90% of the particles pass through on a U.S. standard No. 325 mesh sieve and not more than about 5% of the particles by weight are less than 5 microns. It has been found that amounts of hydrated aluminum oxide from about ¼ to about 10% by weight are most desirable and preferably about 1% by weight of the dentifrice composition.

Various other materials may be incorporated in the oral preparations of this invention. Examples thereof are coloring or whitening agents, preservatives, silicones, chlorophyll compounds, ammoniated materials such as urea, diammonium phosphate and mixtures thereof, and other constituents. These adjuvants are incorporated in the instant compositions in amounts which do not substantially adversely affect the properties thereof.

For some purposes it may be desirable to include antibacterial agents in the compositions of the present invention. Typical antibacterial agents which may be used in amounts of about 0.01% to about 5%, preferably about 0.05% to about 1.0%, by weight of the dentifrice composition include:

$N^1$-4(chlorobenzyl)-$N^5$-2,4-dichlorobenzyl)biguanide;
p-chlorophenyl biguanide;
4-chlorobenzhydryl biguanide;
4-chlorobenzhydrylguanylurea;
N-3-lauroxpropyl-$N^5$-p-chlorobenzylbiguanide
1,6-di-p-chlorophenyl biguanidohexane;
1-(lauryldimethylammonium)-8-(p-chlorobenzyl-dimethylammonium) octane dichloride;
5,6-dichloro-2-guanidinobenzimidazole;
$N^1$-p-chlorphenyl-$N^5$-laurylbiguanide;
5-amino-1,3-bis(2-ethylhexyl)-5-methylhexahydropyrimidine;

and their non-toxic acid addition salts.

Any suitable flavoring or sweetening materials may be employed in formulating a flavor for the compositions of the present invention. Examples of suitable flavoring constituents include the flavoring oils, e.g. oils of spearmint, peppermint, wintergreen, sassafras, clove, sage, eucalyptus, marjoram, cinnamon, lemon and orange, as well as methylsalicylate. Suitable sweetening agents include sucrose, lactose, maltose, sorbitol, sodium cyclamate and saccharine. Suitably, flavor and sweetening agent may together comprise from about 0.01 to 5% or more of the compositions of the instant invention.

The dental creams should have a pH practicable for use. A neutral basic pH is particularly desirable. The initial pH range of about 7 to 9.5 preferably 7.5 is considered the most practicable for use. When reference is made to pH herein, it is intended that such pH determination be made on the dental cream directly. If necessary, basic materials may be added to adjust the pH as desired.

The container in which the dentifrice composition is placed is typically a tube from which the dental cream can be extruded. A particularly desirable aspect of the invention is the fact that the dentifrice composition including insoluble alkali metal metaphosphate can be desirably packaged in an unlined aluminum container and exhibit desirable cosmetic and rheological properties upon storage without causing substantial layer formation or corrosion of the aluminum with which it is contacted.

The most desirable results have been obtained when the dentifrice contains about 0.1 to 3% by weight of insoluble alkali metal metaphosphate and about 44% to 47% by weight of calcium carbonate.

For standardized test purposes in determining the amount of the original monofluorophosphate content present in accelerated aging tests, the dentifrice formulations are prepared with about 0.76% of sodium monofluorophosphate and then tested.

The following specific examples are further illustrative of the nature of the present invention, but it is to be understood that the invention is not limited thereto. The compositions are prepared in the usual manner and all amounts of the various ingredients are by weight unless otherwise specified.

EXAMPLE 1

The following dental creams are prepared:

|  | Parts A | B |
|---|---|---|
| Sodium monofluorophosphate | 0.76 | 0.76 |
| Calcium carbonate | 52.00 | 46.25 |
| Insoluble sodium metaphosphate | — | 1.00 |
| Glycerine | 22.00 | 22.00 |
| Sodium carboxymethylcellulose | 0.95 | 1.30 |
| Hydrated alumina | — | 1.00 |
| Sodium N-lauryl sarcosinate | 2.00 | 2.00 |
| Sodium benzoate | 0.50 | 0.50 |
| Sodium saccharine | 0.20 | 0.20 |
| Flavor | 0.90 | 0.90 |
| Water | q.s. to 100 | q.s. to 100 |

Composition A in which no phosphate salt polishing agent is present and calcium carbonate is the sole abrasive and Composition B containing calcium carbonate, alumina and phosphate salt are aged at 49°C. and the percentage of soluble monofluorophosphate present as fluoride is determined periodically. Each 3 weeks under this aging condition corresponds to about 1 year's aging at room temperature. The results are indicated in the table below:

| | % Soluble Monofluorophosphate as Fluoride—49°C. | | | |
|---|---|---|---|---|
| | WEEKS | | | |
| Composition | 0 | 3 | 6 | 9 |
| A | 0.09 | 0.07 | 0.03 | 0.01 |
| B | 0.09 | 0.08 | 0.08 | 0.07 |

Thus, it is clear from these results that the addition of a small amount of the insoluble metaphosphate and alumina markedly increases the ability of Composition B to retain soluble fluorine.

When composition B is placed in an unlined aluminum tube, the aluminum surface in contact with the dentifrice remains substantially free from corrosion even over a prolonged period of time.

EXAMPLE 2

The following dentifrices also have high retention of soluble monofluorophosphate as fluorine and do not cause a substantial degree of corrosion of the aluminum surface with which they are contacted in unlined aluminum tubes.

| | C | D | E |
|---|---|---|---|
| Sodium monofluorophosphate | 0.76 | 0.76 | 0.76 |
| Calcium carbonate | 40.15 | 44.25 | 47.15 |
| Insoluble sodium metaphosphate | 7.10 | 3.00 | 0.10 |
| Glycerine | 22.00 | 22.00 | 22.00 |
| Sodium carboxymethylcellulose | 1.20 | 1.30 | 1.30 |
| Hydrated alumina | 1.00 | 1.00 | 1.00 |
| Sodium N-lauryl sarcosinate | 2.00 | 2.00 | 2.00 |
| Sodium benzoate | 0.05 | 0.05 | 0.05 |
| Sodium saccharine | 0.20 | 0.20 | 0.20 |
| Flavor | 0.90 | 0.90 | 0.90 |
| Water | q.s. to | q.s. to | q.s. to |

-continued

|  | C | D | E |
|---|---|---|---|
|  | 100 | 100 | 100 |

EXAMPLE 3

The following dentifrices are also within the scope of the invention:

|  | F | G | H |
|---|---|---|---|
| Sodium monofluorophosphate | 0.76 | 0.76 | 0.76 |
| Calcium carbonate | 35.25 | 47.20 | 46.00 |
| Insoluble sodium metaphosphate | 12.00 | 0.05 | 1.00 |
| Glycerine | 22.00 | 22.00 | 22.00 |
| Sodium carboxymethylcellulose | 1.20 | 1.30 | 1.30 |
| Hydrated alumina | 1.00 | 1.00 | — |
| Sodium N-lauroyl sarcosinate | 2.00 | 2.00 | 2.00 |
| Sodium benzoate | 0.50 | 0.50 | 0.50 |
| Sodium saccharine | 0.20 | 0.20 | 0.20 |
| Flavor | 0.90 | 0.90 | 0.90 |
| Water | q.s. to 100 | q.s. to 100 | q.s. to 100 |

EXAMPLE 4

The following dentifrices are prepared:

|  | I | J | K |
|---|---|---|---|
| Glycerine | 22.00 | 22.00 | 22.00 |
| Sodium Benzoate | 0.50 | 0.50 | 0.50 |
| Sodium saccharine | 0.20 | 0.20 | 0.76 |
| Sodium monofluorophosphate | 0.76 | 0.76 | 0.76 |
| Hydrated alumina | — | 52.00 | 1.00 |
| Calcium carbonate | 52.00 | — | 52.00 |
| Sodium carboxymethyl cellulose | 0.95 | 0.95 | 0.95 |
| Sodium N-lauroyl sarcosinate | 2.00 | 2.00 | 2.00 |
| Flavor | 0.80 | 0.80 | 0.80 |
| Water | q.s. to 100 | q.s. to 100 | q.s. to 100 |

Each of the dentifrices are aged at 49°C. with the percentage of monofluorophosphate determined periodically. The results are indicated in the table below:

| Composition | % Soluble Monofluorophosphate as fluoride—49°C. WEEKS | | | |
|---|---|---|---|---|
|  | 0 | 3 | 6 | 9 |
| I | 0.09 | 0.07 | 0.03 | 0.01 |
| J | 0.09 | 0.06 | 0.05 | 0.04 |
| K | 0.09 | 0.08 | 0.07 | 0.07 |

Thus, it is clear that composition K retains soluble fluorine better than compositions I and J.

EXAMPLE 5

The following dentifrices are also within the scope of the invention:

|  | Parts | |
|---|---|---|
|  | L | M |
| Sodium monofluorophosphate | 0.76 | 0.76 |
| Glycerine | 22.00 | 22.00 |
| Sodium benzoate | 0.50 | 0.50 |
| Sodium saccharine | 0.20 | 0.20 |
| Hydrated alumina | 13.00 | 1.50 |
| Calcium carbonate | 39.00 | 52.50 |
| Sodium carboxymethyl cellulose | 0.95 | 0.95 |
| Sodium N-lauroyl sarcosinate | 2.00 | 2.00 |
| Flavor | 0.80 | 0.80 |
| Water | q.s. to 100 | q.s. to 100 |

EXAMPLE 6

The following dentifrices are also within the scope of the invention:

|  | Parts | | |
|---|---|---|---|
|  | N | O | P |
| Sodium monofluorophosphate | 0.76 | 0.76 | 0.76 |
| Calcium carbonate | 35.25 | 42.25 | 44.25 |
| Insoluble Sodium metaphosphate | 12.00 | 5.00 | 3.00 |
| Glycerine | 22.00 | 22.00 | 22.00 |
| Sodium carboxymethyl cellulose | 1.20 | 1.30 | 1.30 |
| Hydrated alumina | 1.00 | 1.00 | 1.00 |
| Sodium N-lauroyl sarcosinate | 2.00 | 2.00 | 2.00 |
| Sodium benzoate | 0.50 | 0.50 | 0.50 |
| Sodium saccharine | 0.20 | 0.20 | 0.20 |
| Flavor | 0.90 | 0.90 | 0.90 |
| Water | q.s. to 100 | q.s. to 100 | q.s. to 100 |

In addition to sodium monofluorophosphate, $Na_2PO_3F$, other monofluorophosphate salts which have sufficient water solubility for use in the instant invention include calcium monofluorophosphate, magnesium monofluorophosphate and aluminum monofluorophosphate. In accordance with this invention the term "monofluorophosphate" also includes monofluoropolyphosphates such as $Na_4P_3O_9F$, $K_4P_3O_9F$, $(NH_4)_4P_3O_9F$, $Na_3KP_3O_9F$, $(NH_4)_3NaP_3O_9F$ and $Li_4P_3O_9F$.

It will be apparent to one skilled in the art that modifications of the above examples may be made thereto.

We claim:

1. A dentifrice composition comprising a water-soluble monofluorophosphate in amount which provides about 0.01–1% by weight fluorine to the dentifrice and about 20–95% by weight of a water-insoluble compatible polishing material consisting essentially of a mixture of calcium carbonate with hydrated alumina; the ratio of said calcium carbonate to said hydrated alumina being about 3:1 to about 1000:1; said dentifrice having an initial pH of about 7 to 9.5.

2. The dentifrice composition claimed in claim 1 wherein said water-soluble monofluorophosphate is sodium monofluorophosphate.

3. The dentifrice composition claimed in claim 2 wherein said polishing agent is present in an amount of about 20% to about 75% by weight of said composition and said composition is a dental cream.

4. The dentifrice composition claimed in claim 2 wherein said monofluorophosphate is present in an amount of about 0.76% by weight.

5. The dentifrice composition claimed in claim 2 wherein the ratio of said calcium carbonate to said alumina is about 3:1 to about 100:1.

6. The dentifrice composition claimed in claim 2 wherein the ratio of said calcium carbonate to said alumina is about 35:1 to about 52:1.

* * * * *